United States Patent [19]
Johnson

[11] Patent Number: 4,763,064
[45] Date of Patent: Aug. 9, 1988

[54] DEVICE FOR MEASURING THE ELECTRONIC CHARACTERISTICS OF SOLID MATERIALS

[75] Inventor: Arthur W. Johnson, Ottawa, Canada

[73] Assignee: Her Majesty the Queen in right of Canada, as represented by the Minister of National Defence of Her Majesty's Canadian Government, Ottawa, Canada

[21] Appl. No.: 34,530

[22] Filed: Apr. 6, 1987

[30] Foreign Application Priority Data

Apr. 18, 1986 [CA] Canada .................................. 506123

[51] Int. Cl.[4] ............................................ G01R 27/02
[52] U.S. Cl. .................................. 324/65 CP; 324/437
[58] Field of Search ................. 204/421; 324/437, 425, 324/446, 447, 448, 449, 450, 57 R, 61 R, 61 P, 65 CP, 65 P

[56] References Cited

U.S. PATENT DOCUMENTS 2,063,840 12/1936 Fairchild et al. ............... 324/65 CP
4,223,077 9/1980 Taylor .................................. 204/421

Primary Examiner—Reinhard J. Eisenzopf
Assistant Examiner—Anthony L. Miele
Attorney, Agent, or Firm—Sheldon Kanars; Edward Goldberg

[57] ABSTRACT

A device for measuring the electronic characteristics of solid electrolytes or solid-state electrochemical cells under varying conditions is provided. The device consists of two small flat plates which provide uniform physical and electrical contact with the material to be measured, a spring for applying pressure to the plates and the material, and electrical connections. The device keeps the plates rigid and parallel, and permits easy temperature measurement and handling.

13 Claims, 1 Drawing Sheet

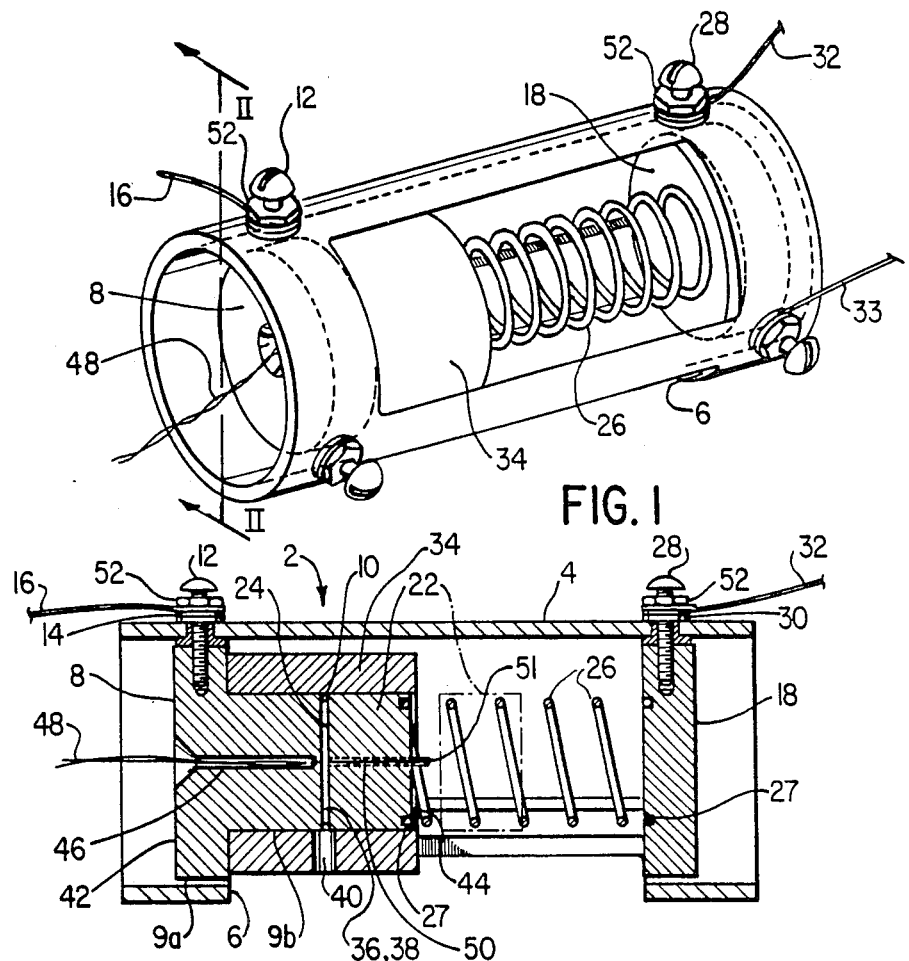
FIG. 1
FIG. 2
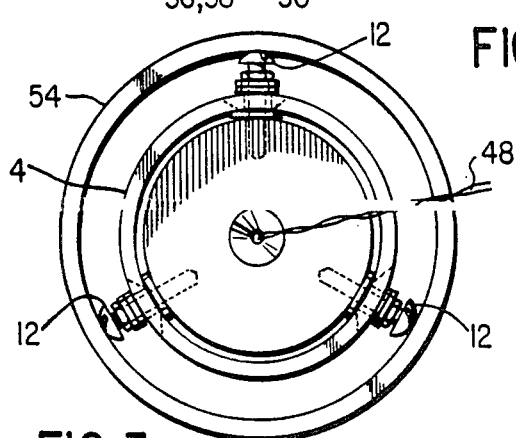
FIG. 3

DEVICE FOR MEASURING THE ELECTRONIC CHARACTERISTICS OF SOLID MATERIALS

FIELD OF THE INVENTION

The present invention relates to a device for measuring electronic characteristics of solid materials such as solid electrolytes and solid-state electrochemical cells.

DESCRIPTION OF THE INVENTION

There is an increasing interest in the development of commercially viable solid-state electrochemical cells or batteries. It has been discovered that polymer electrolytes may be used for high energy density batteries. While only slightly conducting, such electrolytes have been found to provide the necessary characteristics such as high surface-to-thickness ratio and good contact with electrode materials for solid-state electrochemical batteries. At the present time considerable research is being conducted with respect to both electrode and electrolyte materials which can be used and their performance under various conditions such as temperature.

Consequently, there has developed a need to measure the electronic characteristics of such cells, such as the impedance of the solid electrolytes, which are usually in disc or film form, and also the impedance of the interface between the electrolyte and the electrodes. There is also a need to determine the voltametric and potentiostatic behaviour. This information helps to identify and predicate the behaviour of the material under test and, ultimately, the performance of batteries to be made from it. These characteristics can be measured by placing the sample under test in a specially designed cell and by connecting appropriate instrumentatiom, such as an impedance analyser or potentiostat.

The problem of measuring the impedance of solid electrolytes or solid-state electrochemical cells is relatively new compared to known procedures used in wet electrochemistry. The existence of commercial apparatus for this purpose is not known.

Two references in the published literature however are of interest. Firstly, P. Rigaud in a doctoral thesis at the University of Grenoble, France, which thesis was submitted Dec. 1, 1980, and subsequently published, describes and illustrates a test cell for measuring the electrical characteristics of solid electrolytes or solid-state electrochemical cells. The test cell is of complicated design in which the temperature of the sample cannot be accurately measured and the electrical contact to one of the electrodes is uncertain. In addition, because of its construction, the temperature range of operation is restricted to no greater than 150° C. The other reference, a paper by M. Gauthier, et al. published at page 133 in the June, 1985 issue of the Journal of the Electrochemical Society, entitled "Assessment of Polymer-Electrolyte Batteries for EV and Ambient Temperature Applications", describes and illustrates a pair of round electrodes in an inert tube and an unknown method of applying pressure to the cell.

SUMMARY OF THE INVENTION

It is therefore the primary object of the present invention to provide a device for measuring the electronic characteristics of solid materials which is both simple and effective in its operation and which will permit easy adaptation of the conditions of measurement, such as temperature.

In accordance with the present invention there is provided a device for measuring the electronic characterstics of samples of solid materials. The device comprises an elongated tubular retainer frame having a longitudinal axis and cutaway sides for providing access to the interior of the frame. A base plate is secured to the frame near one end thereof. The base plate has an interior surface which is planar and perpendicular to the longitudinal axis of the frame. Means are secured to the base plate within the frame and are adjustable to centre the base plate within the frame. An end plate is secured to the frame near the other end thereof. The device is further provided with a piston, the piston having a forward surface and a rear surface. The piston is urged, when in operation, towards the interior surface of the base plate. A spring means extending between the end plate and the rear surface of the piston urges the piston towards the interior surface of the base plate. The forward surface of the piston is perpendicular to the longitudinal axis of the frame. The sample to be measured is held, during operation, between the interior surface of the base plate and the forward surface of the piston. The piston, spring, end plate and base plate are made of electrically conducting material. Electrical contacts, which are insulated from the frame, are secured to the frame to electrically communicate respectively with the end plate and with the base plate. In this manner there is no electrical contact between the frame and either of these plates. An elongated sleeve fits within the frame and during operation circumscribes the piston, the sample to be measured and a portion of the base plate, to permit longitudinal movement of the piston in a direction parallel to the longitudinal axis of the frame and to maintain lateral stability of the piston. The sleeve is made of an electrically non-conductive material.

In a preferred embodiment of the present invention, specifically directed towards measuring for example the impedance of discs or films of solid electrolytes or the impedence or voltametric or potentiostatic behaviour of solid-state electrochemical cells, the retainer tube and sleeve are of annular shape and the base plate and end plate have circular cross-sections.

The device according to the present invention is both simple to construct and easy to operate. The plates permit a uniform physical and electrical contact with the material being measured and a means of applying appropriate pressure to the material. Appropriate electrical connections for purposes of measurement are provided. The device permits maintaining the plates both rigid and parallel, an important necessary element of any such test device for solid electrolytes or solid-state electrochemical cells. The device may be readily encased in appropriate structures for maintaining different temperatures and lends itself to accurate measurement of the temperature of the sample being measured.

These and other objects and advantages of the invention will become apparent upon reading the following detailed description and upon referring to the drawings.

BRIEF DESCRIPTION OF THE DRAWINGS

FIG. 1 is a perspective view of a test device for cell in accordance with the present invention adapted for measurement of electronic characteristics of solid electrolytes or solid-state electrochemical cells;

FIG. 2 is a cross-section of the device of FIG. 1 along the line II—II; and

FIG. 3 is an end view of the device of FIG. 1.

DETAILED DESCRIPTION OF THE INVENTION

In the following description, similar features in the drawings have been given similar reference numerals.

Turning to the drawings, there is shown an impedance cell 2 for measuring electronic characteristics of solid electrolytes and solid-state electrochemical cells, in accordance with the present invention. The cell comprises an elongated tubular retainer frame 4, illustrated as having an annular cross-sectional shape. Its sides have cut-away portions 6 to provide easy access to the interior of the device. At one end of frame 4 is secured a base plate 8. The base plate is of circular cross-section, having an outer portion 9a of wider cross-sectional area than the inner portion 9b (FIG. 2), inner portion 9b ending at inner surface 10. Inner surface 10 is planar and oriented perpendicular to the longitudinal axis of frame 4. Base plate 8 is adjustably positionable with respect to the interior sides of frame 4, by means of screws 12. Screws 12 are insulated electrically from frame 4 by means of appropriate washers 14 made of an electrically insulating material. An appropriate electrical lead 16 is secured to at least one of screws 12 and communicates, through that screw 12, electrically with base plate 8. Base plate 8 of course is made of an appropriate electrically conductive material such as stainless steel and is electrically insulated from frame 4.

At the other end of frame 4 is secured end plate 18. A piston 22 having an inner surface 24, which during operation is perpendicular to the longitudinal axis of frame 4, is urged longitudinally within frame 4 towards the inner surface 10 of base plate 8, as can be seen in FIG. 2, by means of spring 26. Spring 26, during operation, is held in position by being seated in annular grooves 27 in the interior surface of end plate 18 and the facing surface of piston 22.

Screws 28 are used for securing end plate 18 in position and insulation washers 30 prevent electrical contact between these screws (and hence plate 18) and frame 4. Electrical lead 32 is fixed to at least one of screws 28 securing end plate 18 in position, providing electrical contact to end plate 18. Plate 18, spring 26 and piston 22 are each made of an appropriate electrically conductive material. In this manner, when spring 26 is in position, electrical communication is provided between piston 22 and electrical lead 32. An appropriate ground lead 33 is electrically associated with and secured to frame 4 beneath washer 30 on screw 28, but insulated from screw 28.

Spring 26 provides constant pressure to piston 22. Piston 22 is maintained in lateral alignment, for longitudinal movement, by sleeve 34 which fits snugly on portion 9b of base plate 8. This sleeve may be constructed of polypropylene, boron nitride or some other rigid, non-flowing material which is inert to the sample. Opposite sides of the sleeve may be flattened to allow the sleeve to pass easily through cutaway openings 6 in frame 4. A space 36 between the inner surface 10 of base plate 8 and the inner surface 24 of piston 22, is thereby formed for receiving an appropriate sample 38. The sample would normally be of a solid electrolyte or a solid-state electrochemical cell comprising an electrolyte sandwiched between a cathode and an anode. Vent relief holes 40 are provided in the sleeve 34 adjacent to space 36 to allow for outgassing of the sample, such holes or another small hole extending radially through the sleeve may be used for the placement of a third or reference electrode (not shown) to be embedded in the sample being measured.

The flat surfaces 10 and 24 of base plate 8 and piston 22 respectively are preferably precision ground (RMS surface roughness less than 0.00025 mm) and parallel to within 0.005 mm to permit the thickness of the sample to be measured accurately by a micrometer, both before and after the impedance measurement. For such purpose, additionally, outer surface 42 of base plate 8 and outer surface 44 of piston 22 would be similarly precision ground.

As can be seen in FIG. 2, a central hole 46 may be cut in the outer surface 42 of base plate 8 which hole penetrates to within close proximity (approximately 0.2 mm) of inner surface 10 of base plate 8. A temperature measurement means 48, such as a thermocouple, platinum resistance thermometer element or other sensor is inserted into this hole to measure the temperature of the sample under test.

In addition, a central hole 50 (phantom, FIG. 2) may be drilled in the piston to permit the different placement of a reference electrode 51.

It will be understood that the diameter of portion 9b of base plate 8 may be made slightly larger than that of the piston 22 (phantom, FIG. 2), the sleeve 34 counterbored accordingly to prevent edge shorting of the different elements of a multi-element sample, such as an electrochemical cell having two electrodes and an electrolyte.

In accordance with the present invention, it will be readily understood by one skilled in the art that it is thus possible to measure the impedance of the electrodes, the electrolyte and interfaces between them, and then charge and discharge the cell in the same test assembly.

As can be seen in FIG. 3, the screws 12 and 28 holding respectively base plate 8 and end plate 18 in position in frame 4, may be secured with lock nuts 52 to permit the heads of these screws to be moved inwardly or outwardly with respect to the outer surface of frame 4, thereby holding device 2 in an appropriate container or vessel 54 (FIG. 3) such as a heat resistant glass tube. In this way, appropriate heating or vacuum conditions may be achieved within the container.

The device according to the present invention provides the following desirable features:

(1) Precision ground contacting surfaces with parallel sides to ensure uniform contact with the sample under test. The precision parallel sides permit accurate measurement of the sample thickness.

(2) The ability to locate a temperature sensor in the base plate in close proximity to the sample in order to measure the temperature of the sample accurately and continuously.

(3) An open method of construction which permits the incorporation of a third reference electrode either through one of the vent relief holes 40 in sleeve 34, or in the piston. Sufficient space is available to allow the contacting wire to pass through the spring, in this latter instance. Alternatively the reference electrode may be mounted in the base plate and the temperature sensor in the piston.

(4) An inert machined sleeve which permits longitudinal movement of the piston perpendicular to the base plate and which maintains lateral stability of the piston. The sleeve is mounted on the base plate and supports the piston from it so that all three units are securely positioned. The sleeve also possesses radial holes centred at the position of the sample to allow for degassing of the sample if necessary and to permit, if desired, the mounting of a reference electrode to enter the sample.

(5) A metallic tubular frame to support rigidly and compactly the desired elements of the cell assembly. The cell may be centred in a container or vessel by adjusting the protruding length of the mounting screws at each end of the frame and locking them in place by nuts previously installed. In this way the sample may be uniformly heated by placing the entire unit in the centre of a small heater. The sample may also be outgassed by installing appropriate vacuum connections to the container.

(6) The provision for two-, three-, and four-terminal connections to the cell by insulating the base plate and end plate from the frame and by attaching wires to the mounting screws at appropriate locations with additional nuts and insulating washers.

(7) The provision for a slightly oversized base plate with respect to the piston to obviate the possibility of edge shorting of a cell under test.

(8) The possibility of employing high temperature materials to permit measurements at temperatures above 150° C.

(9) The use of stainless steel for all metallic parts to ensure inertness with respect to the sample and uniformity of dimensional changes due to changes in temperature. If the sample should react with stainless steel then intermediate discs of platinum, for example, may be placed between the stainless steel.

Thus it is apparent that there has been provided in accordance with the invention a device for measuring electronic characteristics of solid materials that fully satisfies the objects, aims and advantages set forth above. While the invention has been described in conjunction with a specific embodiment thereof, it is evident that many alternatives, modifications and variations will be apparent to those skilled in the art in the light of the foregoing description. Accordingly, it is intended to embrace all such alternatives, modifications and variations that fall within the spirit and scope of the invention as set forth in the appended claims.

What is claimed is:

1. A device for measuring electronic characteristics of solid materials comprising an elongated tubular retainer frame having a longitudinal axis and cutaway sides for providing access to the interior of the frame; a base plate secured to the frame near one end thereof, the base plate having an interior surface which is planar and perpendicular to the longitudinal axis of the frame; means for securing and adjustably centring the base plate within the frame; an end plate secured to the frame near the other end thereof; a piston having a forward surface and a rear surface, the piston being urged in operation towards the interior surface of the base plate to secure a sample of solid material therebetween for measurement, a spring means to extend between the end plate and the rear surface of the piston to urge the piston towards the interior surface of the base plate, the forward surface of the piston being perpendicular to the longitudinal axis of the frame; the piston, spring, end plate and base plate being made of electrically conductive material; electrical contacts electrically insulated from the frame being secured to the frame to electrically communicate respectively with the end plate and with the base plate while preventing electrical contact between the frame and either of these plates; and an elongated sleeve to fit within the frame and during operation circumscribe the piston, the sample to be measured and a portion of the base plate to permit longitudinal movement of the piston in a direction parallel to the longitudinal axis of the frame and to maintain lateral stability of the piston, the sleeve being made of an electrically non-conductive material which is inert to the material under test.

2. The device according to claim 1 wherein the retainer tube and sleeve are of annular shape and the base plate and end plate have circular cross-sections.

3. The device according to claim 2 wherein the piston and a portion of the base plate proximal to its interior surface are of similar uniform cross-section and adapted to be received during operation within the sleeve.

4. The device according to claim 2 wherein a portion of the base plate proximal to the base plate interior surface has a diameter slightly greater than that of the piston, and wherein the sleeve is counter-bored at one end to receive this greater diameter.

5. The device according to claim 1 wherein the sleeve is provided with a plurality of spaced vent relief holes extending through its sides to allow for degassing of a material the electronic characteristics of which are being measured.

6. The device according to claim 1 wherein a hole is provided longitudinally through the base plate from its outer end to almost its interior surface, which hole is to receive a temperature measuring means during operation of the device.

7. The device according to claim 1 wherein the means securing the base plate within the frame comprises a plurality of screws spaced about the frame and secured thereto, rotation of the screws serving to laterally adjust the positioning of the base plate within the retainer frame.

8. The device according to claim 6 wherein the screws are further provided with locking nuts associated with the screw and retainer frame, rotation of the screws also serving to vary the height above the outer surface of the retainer frame at which the heads of the screws sit.

9. The device according to claim 1 wherein the means securing the base plate within the frame comprises a plurality of screws spaced about the frame and secured thereto and extending into the base plate, rotation of the screws serving to laterally adjust the positioning of the base plate within the retainer frame, and wherein the means securing the end plate within the frame comprises a plurality of screws spaced about the frame and secured thereto and extending into the end plate, rotation of the screws serving to laterally adjust the positioning of the end plate within the retainer frame.

10. The device according to claim 1 further provided with an electrical ground lead secured to the frame.

11. The device according to claim 1 wherein a small hole extends longitudinally through the piston to receive a reference electrode to be embedded in the sample being measured.

12. The device of claim 1 wherein said device is adapted to measure the impedance of solid electrolytes and solid-state electrochemical cells.

13. The device according to claim 1 wherein a small hole extends radially through the sleeve to receive a reference electrode to be embedded in the sample being measured.

* * * * *